Figure 1:
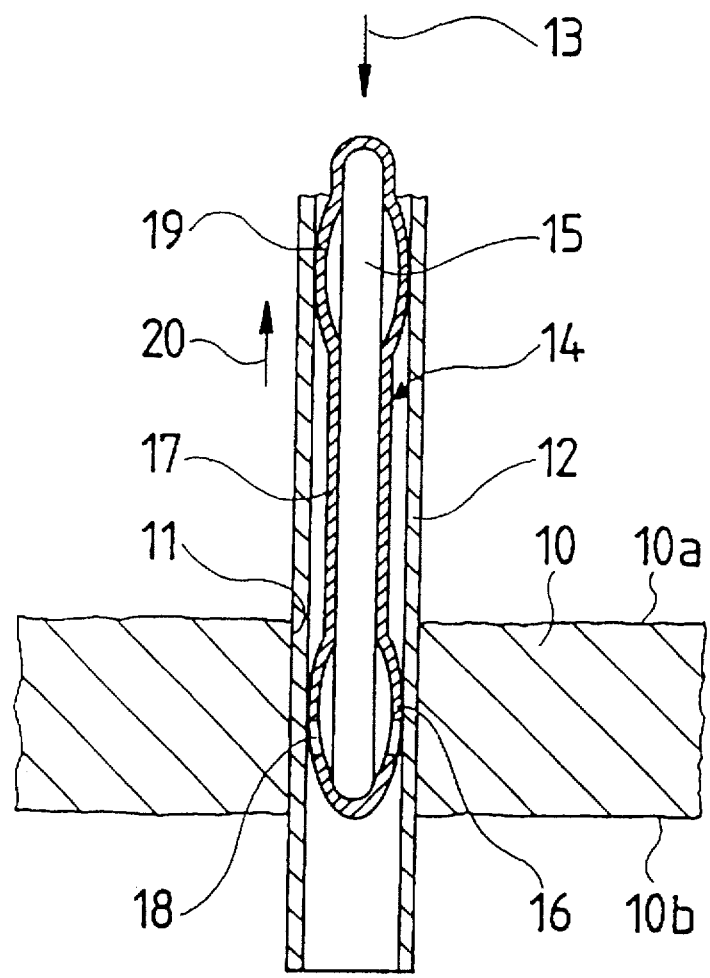

United States Patent [19]
Marx

[11] Patent Number: 5,792,119
[45] Date of Patent: Aug. 11, 1998

[54] TUBULAR IMPLANT TO BE USED FOR PERCUTANEOUSLY FEEDING A PATIENT

[76] Inventor: Karl-Heinz Marx, Bekkamp 5, D-22045 Hamburg, Germany

[21] Appl. No.: 448,352

[22] PCT Filed: Oct. 20, 1993

[86] PCT No.: PCT/EP93/02901

§ 371 Date: Apr. 25, 1995

§ 102(e) Date: Apr. 25, 1995

[87] PCT Pub. No.: WO94/09747

PCT Pub. Date: May 11, 1994

[30] Foreign Application Priority Data

Oct. 27, 1993 [DE] Germany .................. 42 36 210.5

[51] Int. Cl.$^6$ ................................................. A61M 5/00
[52] U.S. Cl. .................. 604/247; 604/175; 604/164; 604/268
[58] Field of Search .................... 604/247, 264, 604/268, 164, 261, 256, 175, 105, 93, 27

[56] References Cited

U.S. PATENT DOCUMENTS

| | | | |
|---|---|---|---|
| 4,393,873 | 7/1983 | Nawash et al. | 604/151 |
| 4,861,334 | 8/1989 | Nawaz | 604/49 |
| 4,863,438 | 9/1989 | Gauderer et al. | 604/247 |
| 4,944,732 | 7/1990 | Russo | 604/247 |
| 4,994,732 | 2/1991 | Russo . | |
| 5,273,529 | 12/1993 | Idowu | 604/49 |
| 5,352,206 | 10/1994 | Cushieri et al. | 604/264 |
| 5,356,382 | 10/1994 | Picha et al. | 604/105 |
| 5,413,565 | 5/1995 | Michels et al. | 604/247 |

FOREIGN PATENT DOCUMENTS

| | | | |
|---|---|---|---|
| 8906529 | 7/1989 | WIPO | 604/247 |
| WO 89/06529 | 7/1989 | WIPO . | |

*Primary Examiner*—Mark O. Polutta
*Assistant Examiner*—Bruce E. Snow
*Attorney, Agent, or Firm*—Vidas, Arrett & Steinkraus, P.A.

[57] ABSTRACT

A tubular implant to be used for percutaneously feeding a patient, which implant is made of resiliently deformable material and includes a distal enlargement adapted to be inserted into the stomach and having at least one opening and a proximally following central tubular section adapted to be inserted into a punctured hole extending from the outside into the stomach cavity, characterized in that the implant includes releasable tensioning or pinching means for reversibly reducing the diameter of the implant along its total length such that it is freely displaceable together with said means through a usual trocar sleeve.

1 Claim, 7 Drawing Sheets

TUBULAR IMPLANT TO BE USED FOR PERCUTANEOUSLY FEEDING A PATIENT

The invention relates to an implant and a set for providing an artificial gastrostomy port.

Implants of this type are being used for long-time gastrostomy feeding of patients. Long-time gastrostomy feeding is necessary when feeding via the mouth and gullet is no longer possible. This may be caused for example by inoperable tumor obstructions of the upper gastrointestinal tract, but also after extensive oral surgery or due to for example neurogenic swallowing difficulties.

In these cases an implant of the above type can be inserted into a punctured hole extending through the abdominal wall to the stomach, and thereafter liquid food can be fed through the implant.

The implants which are known from the literature or are commercially available all are in the shape of a tube having at its distal end an enlargement provided with at least one opening. When implanted this enlargement is seated within the stomach cavity and secures the implant against withdrawal.

The distal enlargement is followed by a central tubular section which extends through the punctured hole outwards. At its proximal end the tubular section is provided with an opening adapted to be closed for example by a plug. Furthermore an outer flange for securing the implant on the abdominal wall can be provided. For the feeding of the patient the implant is opened at its proximal end and is thereafter connected to a food pump via a tube.

In the distal enlargement there can be provided a one-way valve to prevent backflow of the food or flow of stomach fluids into the implant.

Various techniques have become known to insert the implant into the stomach. For a first implantation it is common to pierce a puncture cannula into the stomach and thereafter to insert a guide thread into the stomach through the puncture cannula. The guide thread is engaged by pliers inserted into the stomach through a gastroscope and is withdrawn together with the gastroscope from the mouth. Thereafter the implant is connected to the guide thread, is drawn into the stomach through the mouth and gullet and is inserted into the punctured hole such that the distally enlarged end of the implant engages the inner abdominal wall surface.

The technique as described is relatively complicated (and awsome for the patient) and generally is used only for first implantations when the surgeon cannot use an already existing cured punctured hole. If however a used implant is to be replaced by a new implant, it is usually sufficient to slightly stretch the implant and thereafter withdraw the implant through the already existing punctured hole fixed against displacements of the tissue layers by fusion and, respectively, adhesion. The new implant can be inserted into the stomach in the opposite sequence. For tensioning a rod adapted to be inserted into the implant can be used for example. Such a stretchable implant has become known e.g. from U.S. Pat. No. 5,007,900.

U.S. Pat. No. 3,961,632 discloses a method enabling a first implantation from the outside. In this method a special implant is drawn over the puncture cannula, and the cannula and the implant are inserted into the stomach. Thereafter the cannula is withdrawn, with the implant remaining in the punctured hole and forming an enlargement at its distal area.

However, this known system is disadvantageous in that it requires specially formed implants. Under certain circumstances withdrawal of the cannula from the implant may cause problems, in particular in view of the fact that the implant is held on the cannula only by friction.

The object of the invention is to provide an implant which can be inserted in a simple manner and without too much strain on the patient. A further object of the invention is to provide a set enabling to produce a gastrostomy port in a gentle manner.

In accordance with the invention an implant is provided with tensioning or pinching means for reversibly reducing the diameter of the implant along its total length. When the implant is in a tensioned or pinched condition, it is freely displaceable through a common trocar sleeve along with said means.

Obviously such an implant can be implanted in an optimal manner. It is sufficient to puncture the stomach in a suitable area by a trocar including a trocar sleeve as usually used in the laparoscopy. After the trocar has been removed the implant of the invention can be inserted into the stomach through the trocar sleeve. As soon as this has been done, the trocar sleeve is withdrawn and the tension or pinching means is released from the implant. Thereafter the implant deforms to its operative condition and is ready to be used after the punctured hole has cured.

In one embodiment the tensioning means comprises a stretch rod which is disposed between abutments at the proximal and distal ends of the implant. For deforming the implant to its operative condition it is sufficient to sever the proximal end section carrying the abutment; thereafter the rod can be readily removed. Such an embodiment is relatively inexpensive and easy to be handled.

As an alternative it is possible to press-fit the implant into an elongated plastic tube. This embodiment allows for a particularly effective reduction of the operative diameter. Futhermore, a tube for the implant is to be provided anyhow for sterility reasons, which tube merely would have to be strengthened in the present case. Accordingly also this embodiment can be practised in a cost efficient manner.

In this connection it is of advantage if the plastic tube includes at its distal end a weakening zone allowing to expel the implant out of the tube. To this end the interior of the tube can be coated by a low friction substance. The implant along with the tube, as described above, will be inserted into the punctured hole. Thereafter the implant at its proximal end is secured against displacement in a proximal direction by suitable means such as a rod, and the tube is withdrawn in an outward direction. Thereby the implant, beginning at its distal end, is moved out of the sleeve and can assume its operative shape progressively as it is released from the tube.

As an alternative it is possible to provide a tube having a tear-off thread. By means of the tear-off thread the tube can be opened in the longitudinal direction and thereafter can be withdrawn.

In this implant deformation thereof into the operative condition will produce a proximal outer flange by which the implant is fixed to the abdominal wall. Therafter the implant will be securely retained in the punctured hole on the stomach side by the distal enlargement and on the outside by the flange. Implants having tubular sections of varying lengths are provided for adaptation to differing patient demands, with a suitable implant being selected for the respective purpose. Prior to implantation it is only necessary to measure the length of the punctured hole by common techniques.

Additionally it is possible to provide a retaining plate adapted to be disposed below the flange at the tubular section, which plate ensures an even safer fixing of the implant to the abdominal wall. On the other hand it is possible to keep retaining plates of varying thicknesses in stock in order to be able to adapt an implant of improper length to the length of the punctured hole by selection of a suitable retaining plate.

In a further embodiment such a retaining plate may be pivotally mounted to a plug for closing the proximal opening of the tubular section. An advantage of this embodiment is in particular that the plug can be mounted afterwards. Accordingly the plug which usually is made of a harder material is not contained in the diameter reduced implant thereby facilitating pinching or tensioning thereof.

A further embodiment of the invention relates to the formation of a one-way valve in the distal enlargement. Prior one-way valves use a flap which is disposed in the area of the inlet of the central tubular section within the enlargement. This flap is opened in response to fluid flow in the distal direction and is closed in response to fluid flow in the proximal direction. A disadvantage of such a flap is that it limits reduction of the diameter of the implant during tensioning or pinching thereof so that the implant may become inoperative. Accordingly an embodiment according to claim 9 provides that the one-way valve is formed by an inwardly direction deformation which resiliently engages the inlet of the central tubular section within the enlargement. Such a one-way valve can be readily made of common plastics material and accordingly is particularly inexpensive and easy to be handled because it does not restrict reduction of the diameter of the implant and cannot be dammaged.

Finally the invention relates to a set allowing to produce an artificial gastrostomy port. Such a set consists of a trocar including a trocar sleeve adapted to be inserted into the punctured hole, and an implant. An important prerequisite is that the internal diameter of the trocar sleeve and the external diameter of the tensioned or pinched implant are mated to each other.

In such a set measuring means for determining the length of the punctured hole can be provided to enable the surgeon to select an implant of suitable length; This measuring means allows, prior to the implant being inserted by the trocar sleeve, to insert a probe, to laterally extend a distal abutment thereof ahead of the end of the trocar sleeve, and thereafter to draw the abutment and the trocar sleeve outwardly far enough so that the abutment engages the abdominal wall. As a result the trocar sleeve has its distal end buttwise engage the abdominal wall so that the length of the punctured hole can be precisely determined by means of the scale of the trocar sleeve. The probes can be mechanical probes the abutment of which is for example a pivotal lever, or probes which are in the type of balloon catheters.

The invention will now be described in more detail with reference to a plurality of different embodiments.

Figure 2:
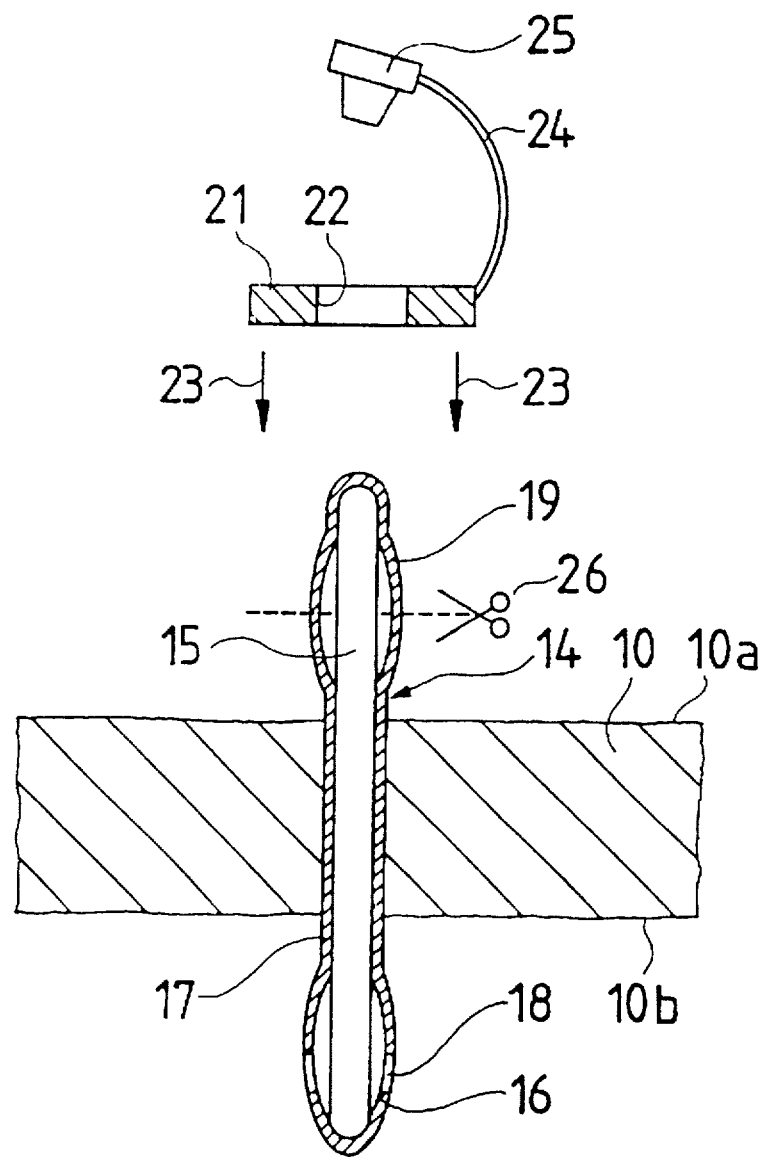
Figure 3:
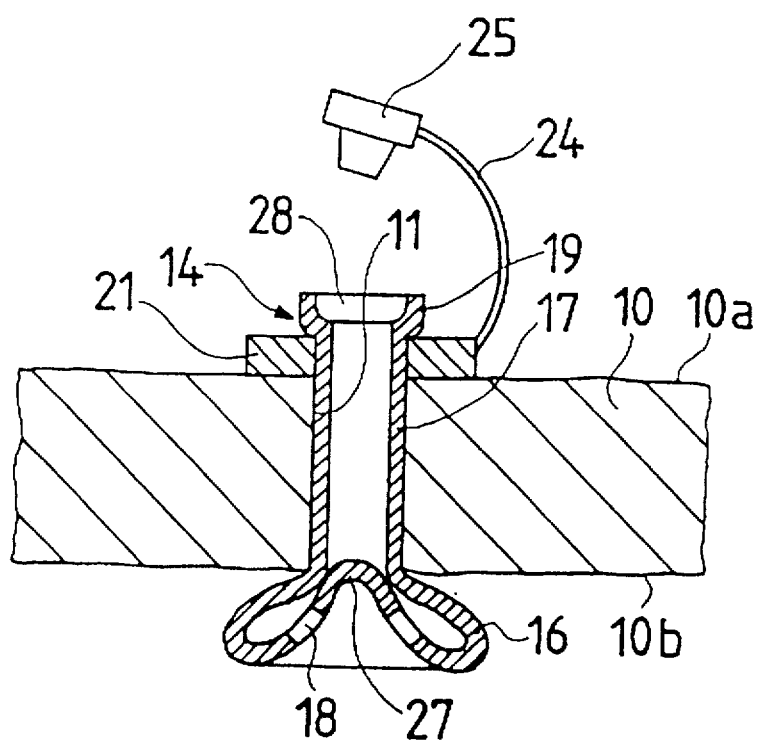
Figure 4:
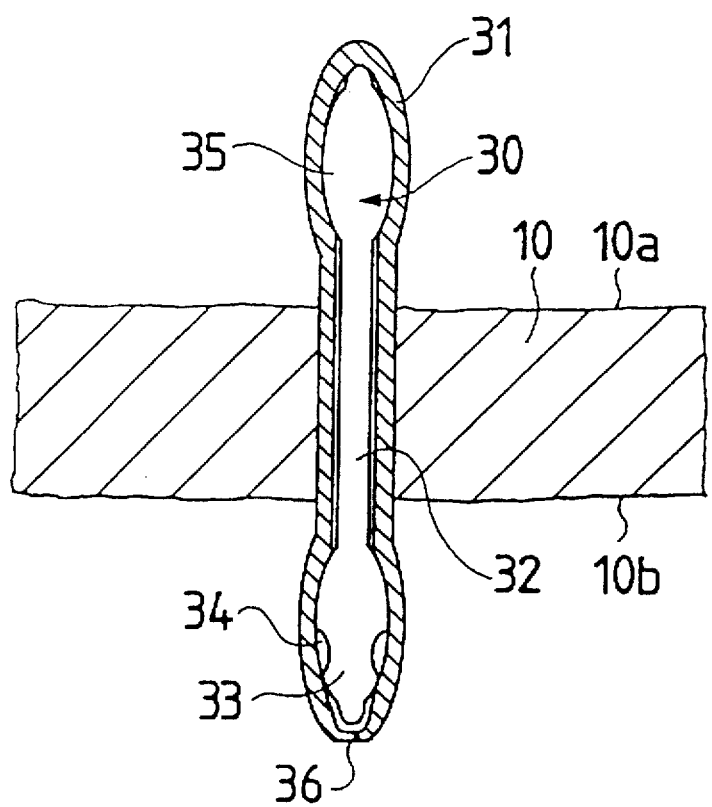
Figure 5:
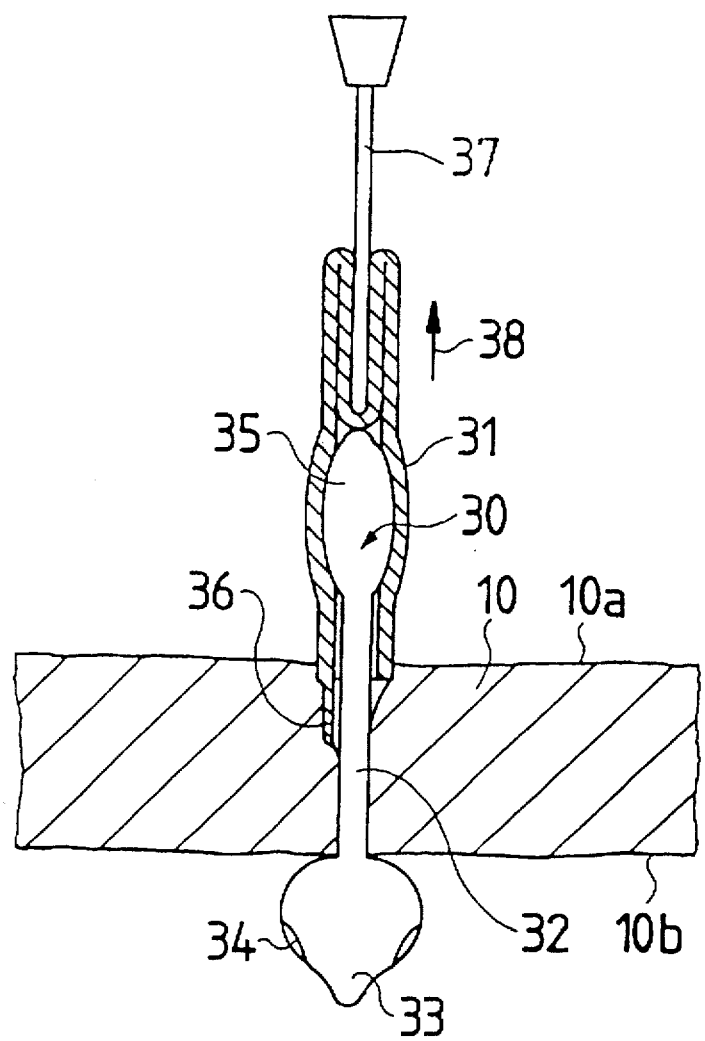
Figure 6:
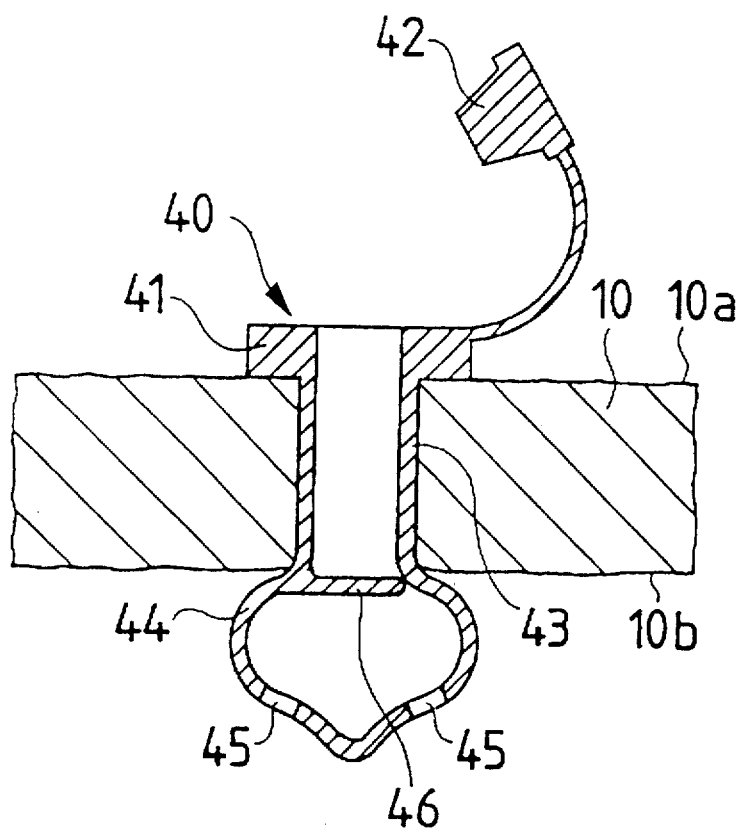
Figure 7:
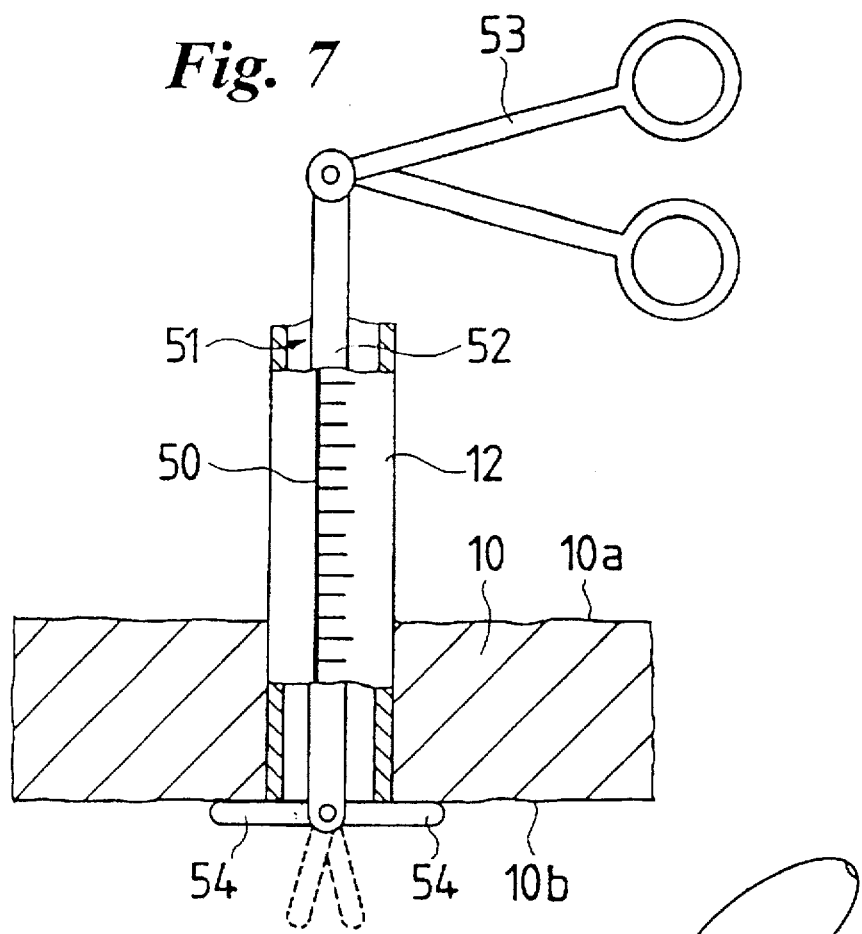
Figure 8:
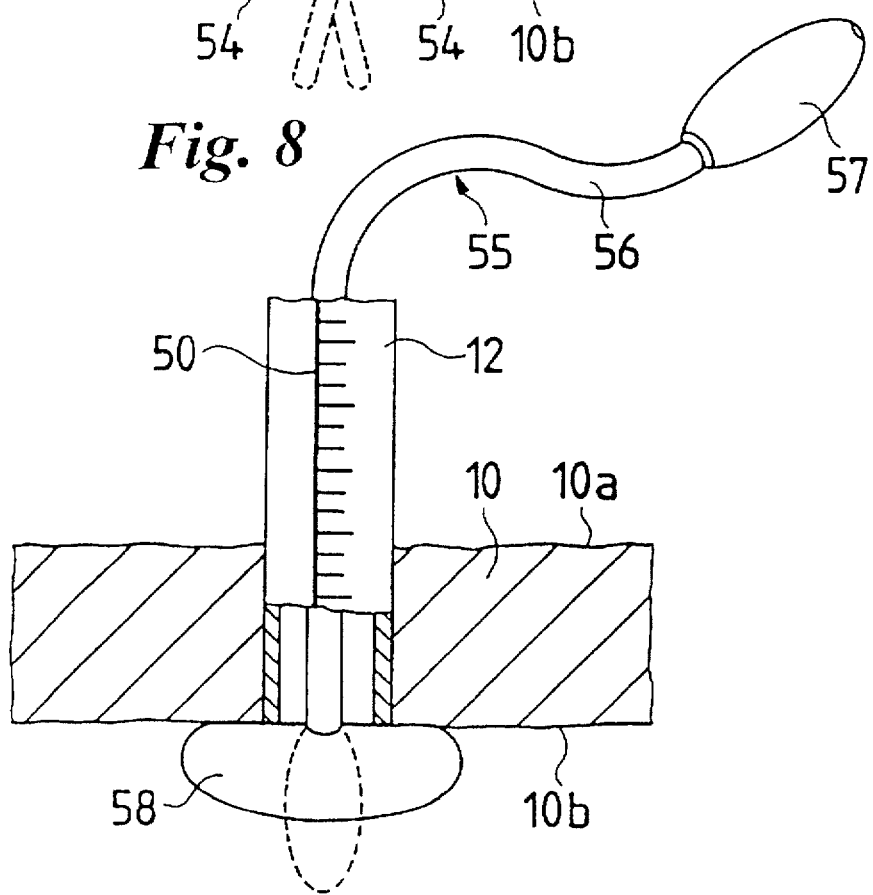

In the drawings:

FIGS. 1 to 3 show a first embodiment of the implant according to the invention in differing conditions of implantation, FIGS. 4 and 5 show a second embodiment during implantation, FIG. 6 shows a third embodiment of the invention in the implanted condition, and FIGS. 7 and 8 show two embodiments of a measuring device for determining the length of the punctured hole.

FIG. 1 is a section through the abdominal wall to show very schematically patient tissue 10 which is limited upwards by the skin 10a and downwards by the inner abdominal wall surface 10b. By means of not shown devices such as a common trocar, a punctured hole 11 through the tissue 10 into the stomach of the patient has been made. A common trocar sleeve 12 has been inserted into this punctured hole 11; as indicated in FIG. 1 by arrow 13 an implant 14 is being inserted through the trocar sleeve towards the stomach. Within the implant 14 there is disposed under tension a stretch rod 15 which deforms the implant 14 into an axially elongated shape so as to reduce its diameter.

The implant 14 has a distal enlargement 16 which follows a central tubular section 17. The distal enlargement 16 includes apertures 18 by which liquid food can be fed into the stomach. Finally the implant 14 has in its proximal end area a flange-like enlargement 19 following the central tubular section 17.

In order to facilitate an understanding of FIG. 2 an arrow 20 has been included in FIG. 1 to indicate that the trocar sleeve 12 is being withdrawn from the punctured hole 11.

FIG. 2 shows the condition when the trocar sleeve 12 has been removed. The tissue 10 now closely encompasses the implant 14 which is still in the shape as shown in FIG. 1.

At this time a retaining plate 21 including a central opening 22 is being moved over the proximal end of the implant 14 to be disposed upon the skin 10a of the patient. A plug 25 is pivotally mounted to the retaining plate 21 by means of a flexible web 24.

After the retaining plate 21 has been positioned, the proximal end of the implant 14 is cut off along the line indicated by the scissors symbol 26, and the stretch rod 15 will be removed.

When the stretch rod 15 has been removed, the implant 14 deforms so as to assume its operative condition as shown in FIG. 3. The central tubular section 17 now extends along the length of the punctured hole 11. The implant 14 is secured against withdrawal by the distal enlargement 16 which engages wall surface 10b. As may be seen the distal enlargement 16 now includes an inwardly directed deformation 27 which resiliently engages the opening of the central tubular section 17. The deformation 17 serves as a one-way valve so as to prevent stomach fluids or liquid food from being discharged to the outside.

Furthermore it may be seen that the retaining plate 21 which has been moved across the proximal end area of the implant 14 is locked on the abdominal wall by the flange-like enlargement 19. Accordingly safe seating of the implant 14 is ensured. Furthermore removal of the stretch rod 15 from the implant 14 at the same time results in the provision of a proximal opening 28 adapted to be closed by the plug 25.

FIGS. 4 and 5 show a further embodiment of the invention. As may be seen in FIG. 4 an implant 30 press-fit into a plastics tube 31 has been inserted into the tissue 10. The condition as shown corresponds substantially to that in FIG. 2, i.e. the trocar sleeve used for implantation has already been removed.

The implant 30 has a central tubular section 32, a distal enlargement 33 provided with apertures 34 and a proximal enlargement 35. In this case the plastics tube 31 is used to reduce the diameter of the implant 30, which tube 31 has a weakening zone 36 at its distal end.

FIG. 5 shows the manner in which the implant 30 is removed from this plastics tube 31 through this weakening zone 36 so as to assume its operative condition. In the embodiment as shown a rod-shaped device 37 is positioned upon the proximal end of the implant, and the plastics tube 31 is withdrawn from the implant in an outward direction along arrow 38. In as much as the tube 31 releases the implant, the latter assumes its operative shape.

Also in this case the implant is opened in the area of the proximal enlargement 35 by a cut and will be locked, if desired, by means of a retaining plate as shown in FIG. 3.

A modified embodiment is shown in FIG. 6. As may be seen an implant 40 has a proximal enlargement 41 which is shaped as a retaining plate. Furthermore a plug 42 is pivotally connected to this retaining plate 41. Such an integral version simplifies surgery, however has the disadvantage that reduction of the diameter of the implant is more difficult.

The plate-like enlargement 41 is followed in the usual manner by a central tubular section 43 which merges into a distal enlargement 44. The distal enlargement 44 includes apertures 45. A one-way valve 46 formed as a flap between the central tubular section 43 and the distal enlargement 44 ensures that fluid flow may occur only in the desired direction from the outside to the inside.

The shown embodiments are merely examples of the invention. As an alternative it is for example possible simultaneously to tension an implant with a stretch rod and to enclose it in a plastics tube. This can be of advantage for example for sterility reasons. Furthermore, it is possible to produce the opening of the plastics tube in another manner such as for example by means of a tear-off thread. Finally the implant can be distributed as a single part or in a set along with a trocar sleeve of suitable diameter. This set may include also means for determining the length of the punctured hole and for generating the access inlet. Such instruments are common in the medical field and accordingly do not need any further description.

Advantageous examples of measuring devices for determining the length of the punctured hole are shown in FIGS. 7 and 8.

FIG. 7 is a section, similar to FIG. 1, of the abdominal wall 10, 10a, 10b including the trocar sleeve 12 which in this case includes a length scale 50 as shown in the - not sectioned - area of the trocar sleeve.

A probe 51 has been inserted through the trocar sleeve 12, which probe is a probe of the type of the usual laparoscope scissors including an elongated shaft 52 and pivotal legs 54 pivotally mounted to its distal end and adapted to be actuated by scissors handles 53. When they are in the retracted position as indicated by dotted lines, they can be inserted through the trocar sleeve 12 into the stomach and thereafter may be pivoted outwards into the extended position as shown by actuation of the scissors handles 53. When in this position the probe 51 is drawn in an outward direction, the pivotal legs 54 engage the distal end of the trocar sleeve 12 so as to draw them outwardly until the pivotal legs 54 engage the wall surface 10b. The trocar sleeve 12 now has its distal end engage buttwise the wall surface 10b. The thickness of the abdominal wall, i.e. that of the tissue 10 between the skin 10a and the wall surface 10b can now be determined by means of the length scale 50.

This allows, in accordance with the measured length of the punctured hole, to select an implant of suitable length so that it may be securely positioned within the punctured hole.

FIG. 8 shows the abdominal wall 10, 10a, 10b and the trocar sleeve 12 of FIG. 7 and a probe 55 of another embodiment.

The probe 55 comprises an elongated resilient tube 56 having at its proximal end pump means for a liquid medium. In the embodiment as shown the pump means is a manual pumping ball 57.

At the distal end of the tube 56 there is provided an inflatable balloon 58 adapted to be inflated from the deflated position which is shown by dotted lines and in which it may be inserted through the trocar sleeve 12, to the inflated position shown by full lines. When the balloon is in the inflated condition, it extends laterally beyond the trocar sleeve 12 and is adapted to move the distal end of the trocar sleeve 12 into buttwise engagement with the wall surface 10 by drawing of the tube 56, in the same manner as described in respect of the probe 51 in FIG. 7.

The two probes 51, 55 of FIGS. 7 and 8 are used to determine the length of the punctured hole in the manner as described and thereafter are removed from the trocar sleeve before the implant is being inserted. For removel of the probe 51 or 55 the abutments 54 and 58, respectively, are brought to a diameter reduced condition by pivoting thereof or, respectively, by pressure release, such that they can be withdrawn through the trocar sleeve.

I claim:

1. A tubular implant to be used for percutaneously feeding a patient, said implant being constructed of resiliently deformable material and includes a distal enlargement adapted to be inserted into the stomach and having at least one opening, said distal enlargement having a distal abutment, a proximally following central tubular section adapted to be inserted into a punctured hole extending from the outside into the stomach cavity, and an enlarged proximal end having a proximal abutment, characterized in that the implant includes a proximal and a distal end and releasable tensioning means comprising a stretch rod which is disposed between and bears against said abutments at the proximal and distal ends of the implant for reversibly reducing the diameter of the implant along its total length such that it is freely displaceable together with said means through a trocar sleeve.

* * * * *